(12) United States Patent
Katoh et al.

(10) Patent No.: US 8,364,416 B2
(45) Date of Patent: *Jan. 29, 2013

(54) INFORMATION PROCESSING SYSTEM USING BASE SEQUENCE RELEVANT INFORMATION

(75) Inventors: Takamasa Katoh, Tokorozawa (JP); Takeo Morimoto, Koshigaya (JP)

(73) Assignee: Hitachi, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/785,188

(22) Filed: May 21, 2010

(65) Prior Publication Data

US 2010/0292975 A1 Nov. 18, 2010

Related U.S. Application Data

(63) Continuation of application No. 10/521,351, filed on Jan. 12, 2005, now Pat. No. 7,747,394.

(30) Foreign Application Priority Data

Jul. 15, 2002 (JP) ................................. 2002-205505

(51) Int. Cl.
*G06F 19/00* (2011.01)
*G06F 15/00* (2006.01)
*G11C 17/00* (2006.01)

(52) U.S. Cl. .................. 702/20; 365/94; 700/1

(58) Field of Classification Search ........................ None
See application file for complete search history.

(56) References Cited

U.S. PATENT DOCUMENTS

| | | |
|---|---|---|
| 5,479,513 A | 12/1995 | Protopopescu et al. |
| 5,970,500 A | 10/1999 | Sabatini et al. |
| 5,985,559 A | 11/1999 | Brown |
| 6,282,656 B1 | 8/2001 | Wang |
| 6,537,747 B1 | 3/2003 | Mills, Jr. et al. |
| 6,874,085 B1 | 3/2005 | Koo et al. |
| 2001/0043217 A1 | 11/2001 | Maloney et al. |
| 2001/0052851 A1 | 12/2001 | Mathias et al. |
| 2002/0010552 A1 | 1/2002 | Rienhoff et al. |

FOREIGN PATENT DOCUMENTS

| | | |
|---|---|---|
| JP | 2000-67139 | 3/2000 |
| JP | 2001-195367 | 7/2001 |
| WO | WO 01/01218 A | 1/2001 |
| WO | WO 01/26029 A | 4/2001 |
| WO | WO 01/28415 A | 4/2001 |
| WO | WO 01/46895 A2 | 6/2001 |
| WO | WO 01/69430 A | 9/2001 |
| WO | WO 02/17190 A1 | 2/2002 |
| WO | WO 02-25519 A1 | 3/2002 |
| WO | WO 02/25528 A1 | 3/2002 |

OTHER PUBLICATIONS

Fuller et al., "Privacy in Genetics Research" Science, vol. 285, No. 5432, pp. 1359-1361, 1999.

Felson et al., "Evidence for a Mendelian Gene in a Segregation Analysis of Generalized Radiographic Osteoarthritis" Arthritis & Rheumatism, vol. 41, No. 6, pp. 1064-1071, Jun. 1998.

Wang, "Security Issues to Tele-medicine System Design" IEEE, pp. 106-109, 1999.

Benkendorf et al., "Patients' Attitudes About Autonomy and Confidentiality in Genetic Testing for Breast-Ovarian Cancer Susceptibility" American Journal of Medical Genetics, vol. 73, pp. 296-303, 1997.

Qiagen Product Guide 2000 (Qiagen Inc., Valencia, CA, 2000, pp. 250-253).

*Primary Examiner* — John S Brusca

(74) *Attorney, Agent, or Firm* — Dickstein Shapiro LLP

(57) ABSTRACT

A highly safe system for processing information includes: (a) receiving requested information for en object and/or service; (b) obtaining positional information in accordance with the requested information from a memory having positional information representing a position in a nucleotide sequence memorized therein and transmitting the obtained positional information; (c) receiving, from among nucleotide sequence-related information associated with positional information, nucleotide sequence-related information corresponding to the positional information transmitted in step (b) and then obtaining semantic information implied by the received nucleotide sequence-related information and/or information associated with the semantic information; and (d) transmitting the semantic information and/or information associated with the semantic information obtained in step (c) in association with the positional information corresponding thereto to the party to which the positional information had been transmitted in step (b).

33 Claims, 7 Drawing Sheets

Fig. 3

| Polymorphism address | .... | Polymorphism Classification | Polymorphism pattern | Classification (name of disease) | Annotative information on the polymorphism pattern (morbidity rate) | Source of information | ...... | Level of disclosure (disclosability) |
|---|---|---|---|---|---|---|---|---|
| 123456 | .... | SNP | A | hypertension | a | ○○ Medical Center (••• Association) | ...... | ○ |
| 123456 | .... | SNP | G | hypertension | b | ○○ Medical Center (••• Association) | ...... | ○ |
| 223456 | .... | SNP | G | large-bowel cancer | (i) | ○○ Medical Center (△△ Cancer Center) | ...... | ○ |
| 223456 | .... | SNP | A | large-bowel cancer | (ii) | ○○ Medical Center (△△ Cancer Center) | ...... | ○ |
| 234567 | .... | SNP | G | stomach cancer | c | ○○ Medical Center (△△ Cancer Center) | ...... | ○ |
| 234567 | .... | SNP | A | stomach cancer | d | ○○ Medical Center (△△ Cancer Center) | ...... | ○ |
| 334567 | .... | SNP | A | asthma | (iii) | ○○ Medical Center (XXX Society) | ...... | ○ |
| 334567 | .... | SNP | G | asthma | (iv) | ○○ Medical Center (XXX Society) | ...... | ○ |
| 345678 | .... | SNP | C | diabetes | e | ○○ Medical Center (••• Association) | ...... | ○ |
| 345678 | .... | SNP | T | diabetes | f | ○○ Medical Center (••• Association) | ...... | ○ |
| 445678 | .... | SNP | T | lung cancer | (i) | ○○ Medical Center (△△ Cancer Center) | ...... | ○ |
| 445678 | .... | SNP | C | lung cancer | (ii) | ○○ Medical Center (△△ Cancer Center) | ...... | ○ |
| 456789 | .... | SNP | T | pollinosis | g | ○○ Medical Center (••• Association) | ...... | ○ |
| 456789 | .... | SNP | C | pollinosis | h | ○○ Medical Center (••• Association) | ...... | ○ |
| : | : | microsatellite | 14 times | immedicable disease | — | ○○ Medical Center (XXX Society) | : | × |
| : | : | microsatellite | 9 times | immedicable disease | — | ○○ Medical Center (XXX Society) | : | × |
| : | : | deletion | G | : | : | ○○ Medical Center (••• Association) | : | ○ |
| : | : | deletion | deletion | : | : | ○○ Medical Center (••• Association) | : | ○ |

| Gno. | Date of birth |
|---|---|
| 0001 | ..**** |

II

| Polymorphism address | Polymorphism pattern | Comment |
|---|---|---|
| 000001 | G | ...... |
| 000002 | T | ...... |
| : | : | : |
| 123456 | A | ...... |
| : | : | : |
| 223456 | G | ...... |
| : | : | : |
| 234567 | G | ...... |
| : | : | : |
| 334567 | G | ...... |
| : | : | : |
| 345678 | C | ...... |
| : | : | : |
| 445678 | T | ...... |
| : | : | : |
| 456789 | T | ...... |
| 456790 | G | ...... |
| 456791 | 14 times | ...... |
| 456792 | deletion | ...... |
| : | : | : |

III

| Anamnesis |
|---|
| infantile asthma |
| gout |
| pollinosis |
| gastric ulcer |
| atopy |
| hypertension |
| diabetes |

IV

| Characteristics | Record |
|---|---|
| blood type | ...... |
| body height | ...... |
| body weight | ...... |
| vision | ...... |
| running ability | ...... |
| psychological test | ...... |
| : | : |

V ......

(clinical record, etc.)

......
......
......
......
......
......
......
......
......

INFORMATION PROCESSING SYSTEM USING BASE SEQUENCE RELEVANT INFORMATION

CROSS-REFERENCE TO RELATED APPLICATIONS

This application is a continuation of U.S. patent application Ser. No. 10/521,351, filed Jan. 12, 2005 now U.S. Pat. No. 7,747,394, the subject matter of which is incorporated in its entirety by reference herein.

FIELD OF THE INVENTION

The present invention relates to an information processing system that provides information through a communication network.

BACKGROUND TECHNIQUE

Currently, genomic nucleotide sequences of various organisms including humans are being rapidly determined and information on genomic nucleotide sequences is being accumulated in various databases. For example, currently in progress is the construction of a system which will enable various research institutes and researchers to utilize information on genomic nucleotide sequences accumulated in databases through an information network such as the Internet.

At the same time, research for the purpose of genomic drug discovery and analysis of genetic information and the like have been actively conducted using nucleotide sequences contained in such information on genomic nucleotide sequences, and differences in nucleotide sequences among individual organisms represented by the single nucleotide polymorphism are attracting attention. In general, differences in nucleotide sequences among individual organisms refer to a polymorphism defined by existence of a predetermined nucleotide difference at a frequency of 1% or more in an individual species and a variation defined by a predetermined nucleotide difference of less than 1% in an individual species. In particular, known polymorphisms are SNP (single nucleotide polymorphism), in which there is one nucleotide difference among individual organisms; an insertion/deletion polymorphism, in which one to several tens of nucleotides (sometimes several thousands of nucleotides) have been deleted or inserted; VNTR (variable number of tandem repeat), in which the number of repetitions of a sequence comprising two to several tens of nucleotides as one unit varies; and a microsatellite polymorphism (a repetition sequence having about two to four nucleotides).

Such polymorphisms sometimes affect, for example, differences in amino acid sequences of proteins among individual organisms or differences in expression efficiency concerning predetermined genes among individual organisms. Such influences cause, for example, differences in the morbidity rate of predetermined diseases among individual organisms or differences in sensitiveness to predetermined medicaments among individual organisms.

A system, however, which provides semantic information useful for each organism among a plurality of individual organisms through effective utilization of differences in nucleotide sequence-related information, such as a polymorphism, is not yet constructed.

DISCLOSURE OF THE INVENTION

Under the above circumstances, the present invention is directed to construction of a highly safe system for processing information for providing semantic information and/or information associated with the semantic information useful for each individual organism through effective utilization of differences in nucleotide sequence-related information among individual organisms.

In the method for processing information on nucleotide sequence according to the present invention, whereby the above objects have been accomplished, a provider of semantic information and/or information associated with the semantic information transmits it in association with the positional information corresponding thereto to the party that presents the nucleotide sequence-related information.

In the method for processing information on nucleotide sequence according to the present invention, whereby the above objects have been accomplished, the party that transmits the nucleotide sequence-related information receives the semantic information implied by the transmitted nucleotide sequence-related information and/or information associated with the semantic information in association with the positional information corresponding to the semantic information and/or information related thereto. In this method, whether or not there is consistency between the received positional information and the transmitted positional information is preferably determined. In this method, when there is no consistency between the received positional information and the transmitted positional information, an alert may be given to the receiver of the nucleotide sequence-related information. In this method, when there is no consistency between the received positional information and the transmitted positional information, information concerning the receiver of the nucleotide sequence-related information may be disclosed to a third party.

The method for processing information on nucleotide sequence according to the present invention can be executed in the form of a program that allows a computer comprising hardware, such as a control unit, a transmitter/receiver, and a memory unit, to execute each step of information processing. The method for processing information on nucleotide sequence according to the present invention can be also executed in the form of a recording medium comprising a program that allows a computer comprising hardware, such as a control unit, a transmitter/receiver, and a memory unit, to execute each step of information processing. Further, the method for processing information on nucleotide sequence according to the present invention can be executed in the form of an information processor comprising hardware, such as a control unit, a transmitter/receiver, and a memory unit, that executes each step of information processing.

This description includes part or all of the contents as disclosed in the description and/or drawings of Japanese Patent Application No. 2002-205505, which is a priority document of the present application.

BRIEF DESCRIPTION OF THE DRAWINGS

FIG. 3 shows an embodiment of data that is recorded in a main database ("database" is hereinafter abbreviated to "DB").

FIG. 5 shows an embodiment of data recorded on a genome-related information recording medium.

DESCRIPTION OF REFERENCE NUMERALS

1: Communication network
2: Shared computer
3: Personal computer

PREFERRED EMBODIMENTS OF THE INVENTION

Hereafter, the present invention is described in detail with reference to the drawings.

A system for processing information that provides a morbidity rate of a predetermined disease to a user is described as an embodiment to which the present invention has been applied. Specifically, it is described with reference to the case where a user "requests an object and/or service," such as his/her morbidity rate relating to a predetermined disease. The present embodiment is directed to explaining a system for processing information that can perceive unauthorized use and acquisition of nucleotide sequence-related information. For the convenience of explanation, this system is explained as a simple model. "An object and/or service" is not limited to the aforementioned, and it includes, for example, objects such as pharmaceutical products, foods, and nonessential grocery items that suit individuals' (individual organisms') diatheses and services such as information that suits individuals' (individual organisms') diatheses and properties.

Figure 1:
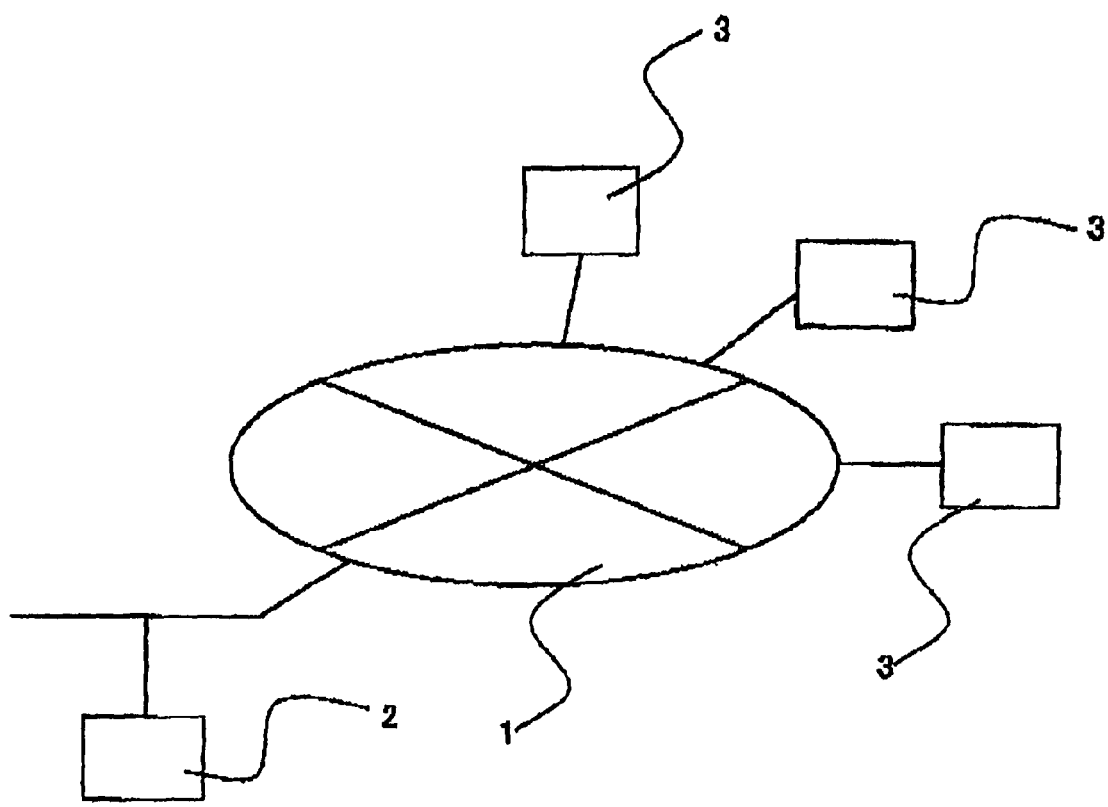
FIG. 1 schematically shows a construction of a system for processing information to which the present invention has been applied.

As shown in FIG. 1, the system for processing information comprises a communication network 1, such as the Internet, a shared computer 2 connected to communication network 1, and a plurality of personal computers 3 connected to communication network 1, and enables data communication between shared computer 2 and personal computers 3 through communication network 1.

Figure 2:
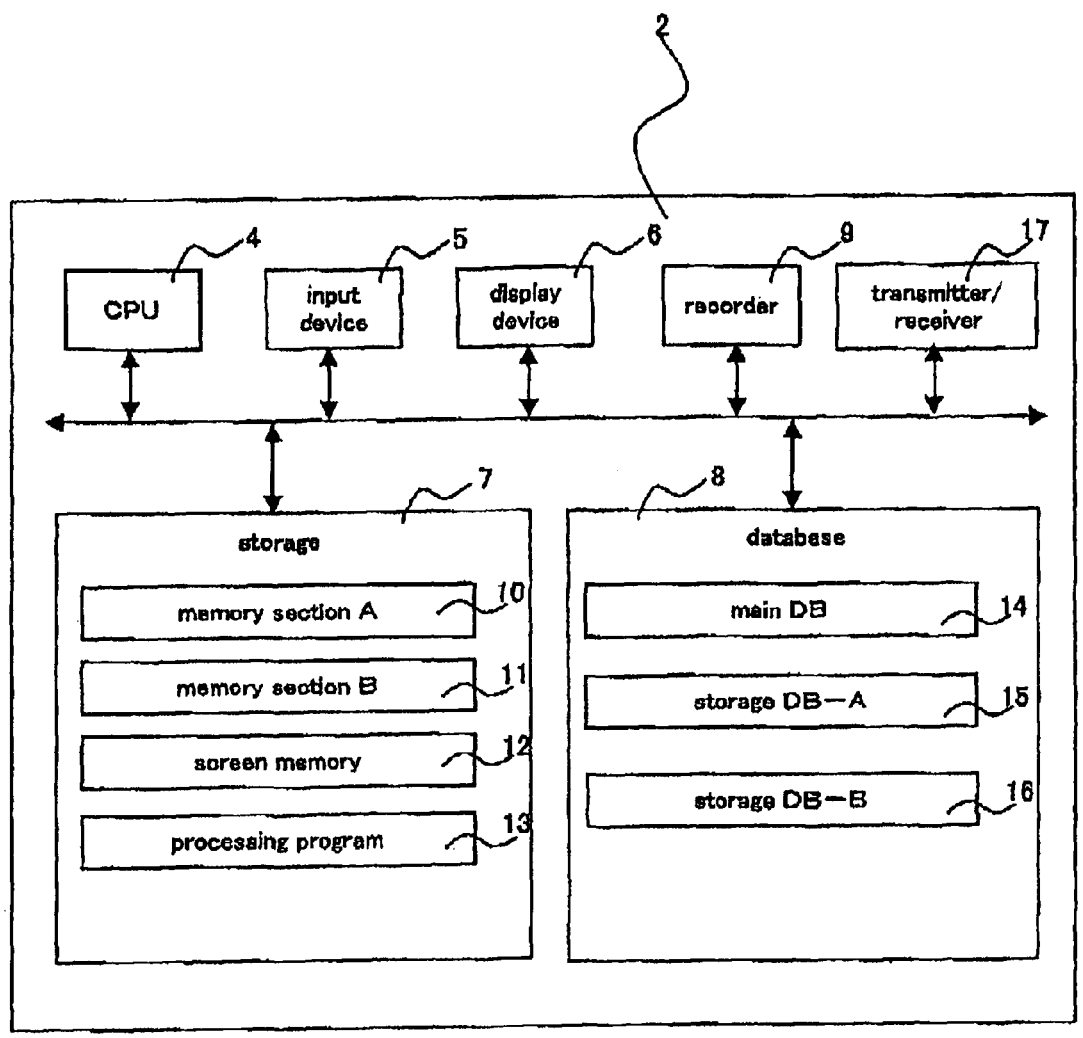
FIG. 2 schematically shows a construction of a shared computer.

As shown in FIG. 2, shared computer 2 is constituted by a CPU 4 that totally controls the operation of the shared computer 2; an input device 5, such as a keyboard and a mouse, with which information, instructions for executing a program and the like can be input; a display device 6 such as a display apparatus; a storage 7 in which temporary information, unrewritable information and the like are recorded; a database 8 for storing various data; a recorder 9 for writing predetermined information in storage 7 and database 8; and a transmitter/receiver 17 for transmission and reception of information to and from personal computers 3 through communication network 1.

Storage 7 in shared computer 2 is constituted by a memory section A10 and a memory section B11 which respectively record different types of information; a screen memory 12 having recorded therein screen data displayed, for example, on personal computer 3 or display device 6; and a processing program 13 for operating the system. Shared computer 2 may have screen memory 12, processing program 13 and the like in an external recording apparatus (not shown) connected to shared computer 2 through communication network 1 instead of containing those in storage 7 inside shared computer 2.

Database 8 (described as "memory" in Claim) in shared computer 2 is constituted by a main DB 14 in which a polymorphism address, a polymorphism pattern, and semantic information are recorded; a storage DB-A15 for saving information recorded in memory section A10; and a storage DB-B16 for saving information recorded in memory section B11. As shown in FIG. 3, polymorphism addresses, a plurality of possible polymorphism patterns in the polymorphism address respectively, and semantic information implied by each of the plurality of polymorphism patterns respectively are stored in association with one another in main DB 14. Main DB 14 may also have recorded therein semantic information implied by a combination of polymorphism patterns in a plurality of polymorphism addresses (such as haplotype).

The "polymorphism address (positional information)" refers to, at least, a position in a nucleotide sequence where a polymorphism is present. In general, the term "polymorphism" includes, for example, a so-called SNP (single nucleotide polymorphism), RFLP (restriction fragment length of polymorphism), VNTR (variable number of tandem repeat), and microsatellite. However, the term "polymorphism" used herein is not limited to these and also includes a variation in nucleotides and nucleotide sequences existing only at a frequency of less than 1% in an individual species. Therefore, "polymorphism address" also includes a position in a nucleotide sequence which indicates a variation of a nucleotide and nucleotide sequences existing only at a frequency of less than 1% in an individual species. Specifically, the "polymorphism address" indicates a position representing a polymorphism or the like by a combination of numerical values, letters, symbols, and the like. The polymorphism address is not particularly limited, for example, may be represented by a combination of a chromosome number, a symbol indicating a gene having a polymorphism therein, and a numerical value indicating a position of a polymorphism in the gene. Alternatively, it may be a combination of a symbol indicating a gene having polymorphism therein and a numerical value indicating a position of polymorphism in the gene.

Further, a "polymorphism address" may be a notation peculiar to a polymorphism imparted to each polymorphism. When the notation peculiar to a polymorphism is used as a polymorphism address, the polymorphism address does not directly indicate the position in the nucleotide sequence, instead, the position can be indirectly found by the notation peculiar to the polymorphism. Therefore, the "polymorphism address" includes the notation peculiar to the polymorphism. A "polymorphism pattern (nucleotide sequence-related information)" is information on nucleotide sequences which differ among individual organisms, and contains, at least, a pattern of nucleotides or nucleotide sequences in a polymorphism. In addition, the "polymorphism pattern" includes a pattern of nucleotide and nucleotide sequences existing only at a frequency of less than 1% in an individual species and is not limited to a polymorphism. For example, in a polymorphism address known to have A or G, the "polymorphism pattern" is represented either by "A" or "G".

The "polymorphism pattern" may represent a heterozygote or homozygote in a homologous chromosome. For example, the "polymorphism pattern" can be represented by "AA", "GG", or "AG" in the polymorphism address known to have A or G.

Further, the "polymorphism pattern" may indirectly represent a possible pattern in the predetermined polymorphism address instead of direct representation of patterns. For example, in the polymorphism address known to have A or G the "polymorphism pattern" may be represented by "allele 1" when the polymorphism address has "A" or "allele 2" when the polymorphism address has "G". As described above, when the "polymorphism pattern" can be expressed as "AA", "GG", or "AG", the "polymorphism pattern" may be represented by "α" when expressed as "AA", it may be represented by "β" when expressed as "GG", and it may be represented by "γ" when expressed as "AG". The polymorphism pattern may or may not be encrypted in this system.

When the polymorphism is the microsatellite type the "polymorphism pattern" may be represented, for example, by numerical values indicating "the number of repetitions" and when the polymorphism is the insertion/deletion type the "polymorphism pattern" may be represented, for example, by symbols indicating "presence/absence". The "polymorphism pattern" in each polymorphism address may be represented by, for example, "polymorphism 1," "polymorphism 2," or "polymorphism 3," in accordance with given rules and arrangements. For example, it can be represented by "polymorphism 1," "polymorphism 2," or "polymorphism 3," in descending order of frequency regarding the "polymorphism pattern" that can appear in each polymorphism address. In this case, "polymorphism 1" in a polymorphism address is not always the same as that in other polymorphism addresses. Specifically, "polymorphism 1" in a given polymorphism address represents "AA" that can appear with the highest frequency, and "polymorphism 1" in other polymorphism addresses represents "GG" that can appear with the highest frequency.

The term "semantic information" used herein refers to information associated with the "polymorphism pattern," for example, information including responsiveness to medicaments, side-effect caused by medicaments, a risk against diseases and disorders, diatheses and properties, interaction among proteins, and various phenotypes caused by differences in polymorphism patterns. "Semantic information" may directly represent a variety of phenotypes resulting from differences in "polymorphism patterns." Alternatively, it may indirectly represent phenotypes with the use of symbols that indicate such phenotypes or the like. "Semantic information" is a type of information which is corrected and increases in the numbers of types accompanied by progress in research on genome and genetics, and constant updating is preferred. In other words, "semantic information" becomes more accurate through increases and decreases in the amount of information accumulated by updating a database using the results of research on genome and genetics, Information that is further induced from "semantic information" is "information associated with the semantic information" although it is not directly associated with the "polymorphism pattern." When "semantic information" is a risk against diseases, when the relevant risk exceeds a given standard, for example, specific "medical examination items" are derived. These specific "medical examination items" are "information associated with the semantic information."

In the present embodiment, semantic information is recorded in main DB 14 as "annotative information on the polymorphism pattern" associated with at least the predetermined "polymorphism address" and "polymorphism pattern" as shown in FIG. 3. Also, semantic information is associated with, for example, "polymorphism classification," "classification (name of disease)" and the like corresponding to the predetermined "polymorphism address." Consequently, when a predetermined "polymorphism address" is a predetermined "polymorphism pattern," types of diseases and annotative information (semantic information) on the morbidity rates of diseases can be obtained. For example, semantic information can be associated with a combination of respective polymorphism patterns corresponding to a plurality of polymorphism addresses (such as haplotype). In other words, each combination of polymorphism patterns in a plurality of polymorphism addresses can be respectively associated with annotative information (semantic information) representing different morbidity rates for predetermined diseases. In this case, when a plurality of polymorphism addresses are a combination of predetermined polymorphism patterns, annotative information (semantic information) indicating the morbidity rate of a predetermined disease can be obtained.

Semantic information can be further associated with a "level of disclosure" which is set in accordance with a predetermined standard. For example, a standard in setting a "level of disclosure" can be determined by taking into consideration unpredictable disbenefits and the like for individuals that would be caused by disclosure of semantic information, i.e., the morbidity rate of "classification (name of disease)". In particular, in shared computer 2, a "level of disclosure" can be set such that semantic information, the disclosure of which is inappropriate from the view point of for example, law, regulations, the behavioral norms of an organization having the shared computer 2 or a contract with the user, is not disclosed. In this case, with this system, annotative information representing a morbidity rate associated with a "level of disclosure" at which disclosure is not possible is not disclosed to users. This can prevent the provision of semantic information which could result in unpredictable disbenefit for users or the disclosure of semantic information to parties other than the contract party As shown in FIG. 3, information concerning the source of semantic information is associated with the semantic information as the "source of information." This "source of information" indicates the origin of semantic information, such as the organization that had produced the semantic information or the organization that had provided the semantic information to shared computer 2. Credibility of semantic information or the like can be evaluated by associating the "source of information" with the semantic information.

In database 8, for example, data such as nucleotide sequence-related information that is the genetic information of the individual requester utilizing the system can be recorded in storage DB-B16. In storage DB-A15, for example, data such as information distinguishing the requester from others utilizing the system can be recorded. In this way, the separate recording of the genetic information of individuals and the information for specifying individuals in storage DB-A15 and storage DB-B16, respectively, makes it difficult to associate a user's genetic information with data that specifies the user.

Shared computer 2 is not limited to one having database 8 therein, and it may have an external database (not shown) connected to shared computer 2 through communication network 1. Shared computer 2 may have a plurality of databases 8 therein or may have an internal database 8 and an external database connected to shared computer 2 through communication network 1.

Figure 4:
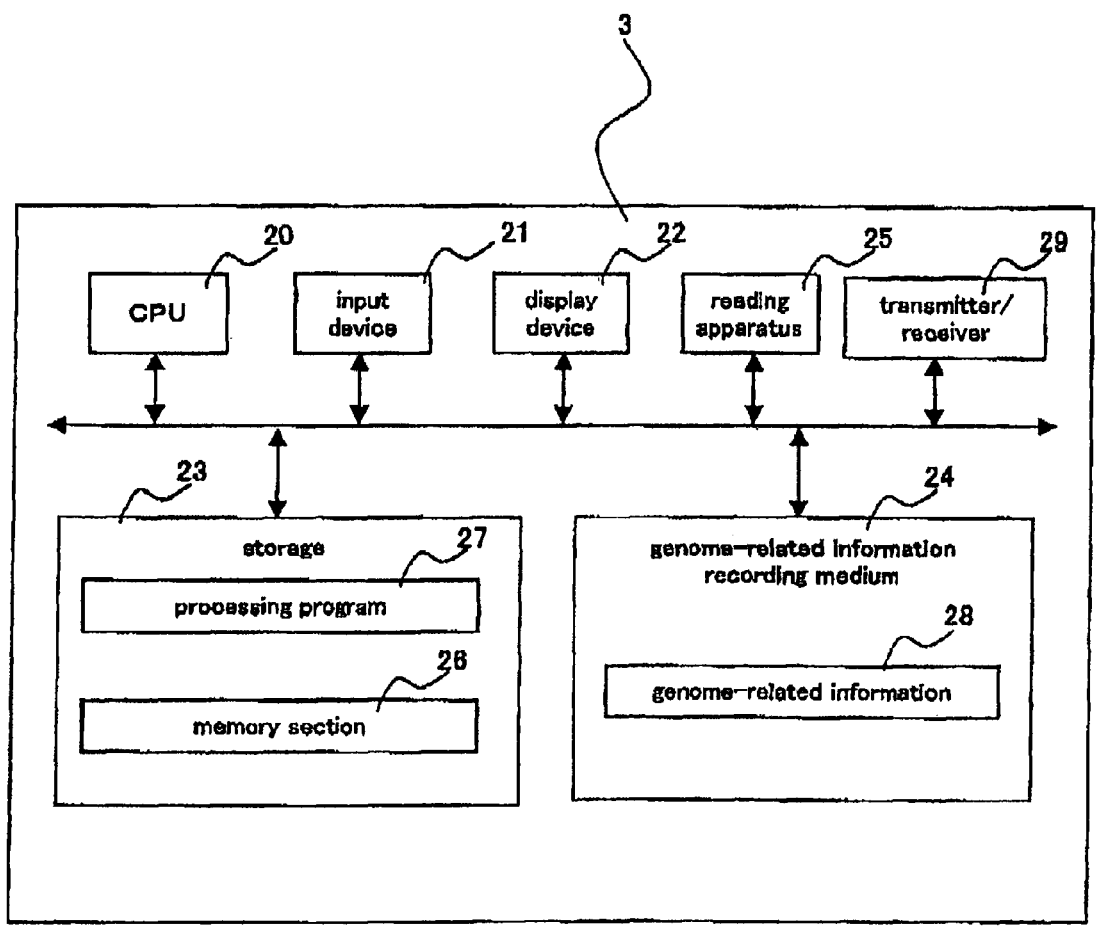
FIG. 4 schematically shows a construction of a personal computer.

As shown in FIG. 4, personal computer 3 is constituted by CPU 20 that totally controls operation of personal computer 3, input device 21 such as a keyboard and a mouse with which information and instructions for executing a program are input, display device 22 such as a display apparatus, storage 23 having temporary information, rewritable information and the like recorded therein, reading apparatus 25 for reading data from genome-related information recording medium 24, and transmitter/receiver 29 for transmitting and receiving information to and from shared computer 2 through communication network I. Personal computer 3 is not limited to a commonly used computer. For example, it may be any form of cellular phone, personal digital assistance, or other mobile communication tool.

Storage 23 in personal computer 3 has a memory section 26 for recording information provided from genome-related information recording medium 24 and the like, and is recorded a processing program 27 for operating the system for processing information.

Genome-related information recording medium 24 has genome-related information 28 of an individual recorded thereon. Genome-related information recording medium 24 includes, for example, a magnetic recording medium such as a magnetic disk or a magnetic card, an optical recording medium employing such as a magneto-optic recording system or a phase-change recording system, and a semiconductor memory. This genome-related information recording medium 24 may be in any form such as, for example, card, disk, stick, tape, or drum. Further, this genome-related information recording medium 24 may comprise genome-related information 28 of a single individual (an individual organism) recorded thereon. Alternatively, it may comprise a plurality of pieces of genome-related information 28 on a plurality of individuals (individual organisms) recorded thereon.

Genome-related information 28 contained in genome-related information recording medium 24 refers to, at least, a "polymorphism address" and a "polymorphism pattern" in the predetermined polymorphism address obtained as a result of analysis of an individual's (individual organism's) nucleotide sequences. Genome-related information 28 may contain various information, such as information concerning anamnesis, characteristics, an individual's clinical record, or a result of medical examination.

On genome-related information recording medium 24, recorded as genome-related information 28 is, for example, as shown in FIG. 5, the individual's number "Gno." (G number) peculiar to genome-related information 28 as well as the individual's information, such as date of birth, as data I; polymorphism addresses and polymorphism patterns as data H; anamnesis information as data III; characteristics as data IV; and information concerning the individual's clinical record and the like as data V. In other words, genome-related information 28 is constituted by data I, data II, data III, data IV, and data V. Data I and data II contain essential information and data III, data IV, and data V are respectively constituted by additional information.

In genome-related information 28, the "polymorphism address" corresponding to the position on the nucleotide sequence is linked with the "polymorphism pattern" in the polymorphism address and recorded. Additional information in a predetermined polymorphism address may be recorded in data TI as a "comment" linked with a "polymorphism address". All the nucleotide sequences of a predetermined individual organism may be recorded in data II. Even when all the nucleotide sequences are recorded in data II, "polymorphism addresses" and "polymorphism patterns" are contained within data H.

According to the present invention, personal computer 3 and genome-related information recording medium 24 are not limited to the construction as shown in FIGS. 4 and 5 respectively. For example, a genome-related information recording medium may be equipped with a memory section having a processing program and a personal computer may have the genome-related information recording medium mounted thereon to operate the processing program. In this case, a personal computer can be operated in accordance with a processing program recorded in a memory section on a genome-related information recording medium.

Figure 6:
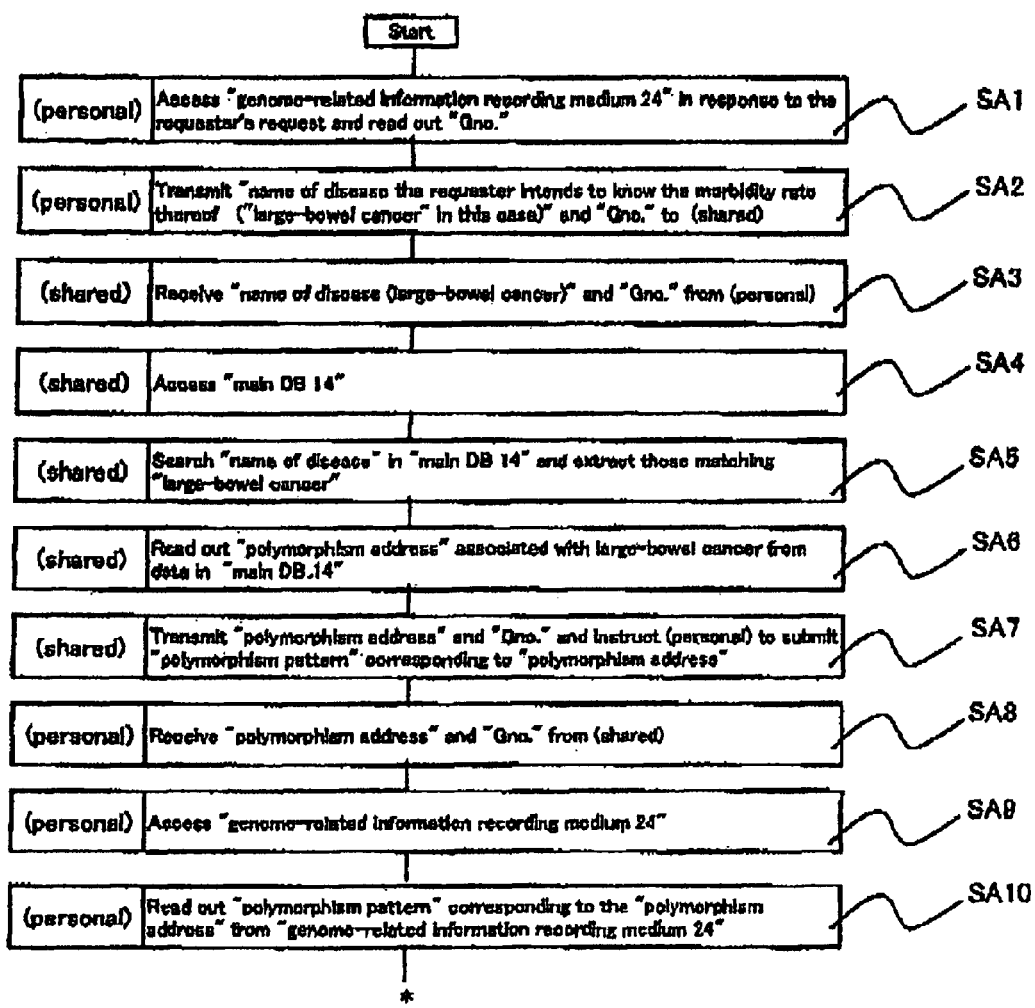
FIG. 6 is a flow chart showing the process in a shared computer and that in a personal computer in a system for providing a morbidity rate of a predetermined disease.
Figure 7:
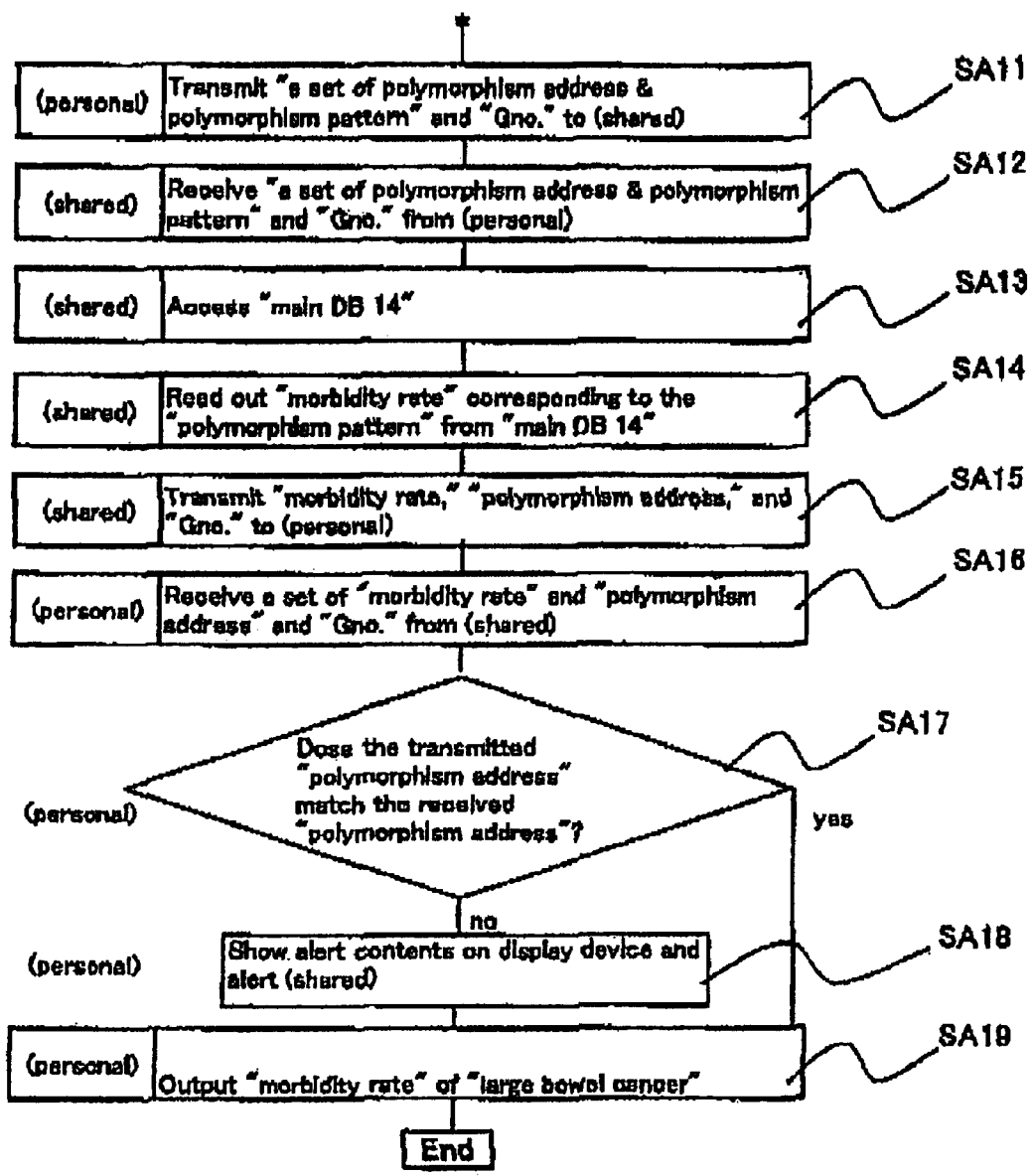
FIG. 7 is a flow chart, which is a continuation of FIG. 6, showing the process in a shared computer and that in a personal computer in a system for providing a morbidity rate of a predetermined disease.

In a system for processing information having the above construction, processing program 13 recorded in storage 7 in shared computer 2 and processing program 27 recorded in storage 23 in personal computer 3 process information in accordance with, for example, flow charts as shown in FIGS. 6 and 7. In the flow charts as shown in FIGS. 6 and 7, a step described as "(shared)" refers to processing in shared computer 2 and a step described as "(personal)" refers to processing in personal computer 3.

The system for processing information is a system in which an individual possessing genome-related information recording medium 24 accesses shared computer 2 using personal computer 3 through communication network 1 and utilizes semantic information recorded in main DB 14 in shared computer 2. The system for processing information may be a system comprising the genome-related information recording medium 24, having genome-related information 28 on a plurality of individuals recorded thereon, to which individuals respectively access.

An individual utilizing this system possesses, for example, genome-related information recording medium 24. An individual utilizing this system (hereafter referred to as a "requester") first starts processing program 27, which is recorded in storage 23, in step A1 (SA1). Processing program 27 drives reading apparatus 25 in personal computer 3 to access genome-related information recording medium 24. Thus, "Gno." recorded as data I on genome-related information recording medium 24 is read out and the read-out "Gno." is stored in memory section 26.

In step A2 (SA2), based on a screen image displayed by processing program 27 on display device 22, information, the provision of which is desired by the requester wishes to receive, for example, the "morbidity rate of large-bowel cancer" (requested information), is input to personal computer 3. At the same time, the "morbidity rate of large-bowel cancer" and "Ono." are transmitted to shared computer 2 from personal computer 3 through communication network I. Alternatively, the requester writes the "morbidity rate of large-bowel cancer" and "Gno." in shared computer 2 from personal computer 3 through communication network 1.

In step A3 (SA3), shared computer 2 receives the "morbidity rate of large-bowel cancer" and "Gno." The received "morbidity rate of large-bowel cancer" and "Ono." are stored in memory section A10 as request information.

In step A4 (SA4), upon the reception of request information, processing program 13 recorded in storage 7 is started to access main DB 14. This processing program 13 performs processing in shared computer 2.

In step A5 (SA5), in accordance with processing program 13, "classification (name of disease)" recorded in main DB 14 is searched and information matching with the requested "morbidity rate of large-bowel cancer" (large-bowel cancer) is extracted.

In step A6 (SA6), from among data recorded in main DB 14, a "polymorphism address" associated with "classification (name of disease)" (large-bowel cancer) that matches with the "morbidity rate of large-bowel cancer" is read out. The read-out "polymorphism address" is stored as positional information associated with request information in memory section A10. Specifically, the "morbidity rate of large-bowel cancer" and "polymorphism address" are recorded in memory section A10 in association with a predetermined "Gno."

In step A7 (SA7), "Gno." and "polymorphism address" recorded in memory section A10 are transmitted to personal computer 3 and instruction information instructing submission of a "polymorphism pattern" corresponding to the transmitted "polymorphism address" is transmitted to personal computer 3. At this time, the submission of additional information such as that concerning anamnesis and characteristics may be optionally instructed depending on the types of request information.

In step A8 (SA8), "Gno.," "polymorphism address," and instruction information transmitted from shared computer 2, are received. The received "Gno." and "polymorphism address" are recorded in memory section 26.

In step A9 (SA9), data II recorded on genome-related information recording medium 24 is accessed in accordance with the received instruction information. In step A10 (SA10), in accordance with processing program 27, data II recorded on genome-related information recording medium 24 is searched, a polymorphism pattern in the instructed polymorphism address is read out, and the polymorphism pattern is then recorded in memory section 26 in association with the polymorphism address. In this case, whether the "Gno." received in step A8 is correct or not is preferably confirmed by accessing data I. In step A10, additional information recorded in data III, data XV, and data V is read out simultaneously with the polymorphism pattern and may be optionally recorded in memory section 26.

In step A11 (SA11), the temporarily-recorded polymorphism pattern associated with the polymorphism address and the optionally-recorded additional information in memory section 26 are output to shared computer 2 together with "Ono." through communication network 1. In step A12 (SA12), shared computer 2 receives the polymorphism pattern associated with the polymorphism address and the optionally-recorded additional information, and the received polymorphism pattern is recorded in memory section A10 in association with the polymorphism address.

In this embodiment, in step A7 shared computer 2 transmits instruction information instructing submission of the "polymorphism pattern", and in step A10 personal computer 3 reads out the polymorphism patterns from genome-related information recording medium 24 in accordance with instruction information. The system, however, may not transmit the instruction information in step A7. In this case, personal computer 3 searches data II in step A10 based on the polymorphism address received in step A8 and reads out polymorphism patterns of the received polymorphism address in accordance with processing program 27. Then, in step A11, personal computer 3 outputs polymorphism patterns and the like to shared computer 2. Also in this case, in step A12 shared computer 2 can obtain the polymorphism pattern of the "polymorphism address" associated with "classification (name of disease)" that matches the "morbidity rate of large-bowel cancer".

In step A13 (SA13), main DB 14 is accessed to search information matching with the received polymorphism address and polymorphism patterns. More specifically, a plurality of polymorphism patterns are recorded in main DB 14 for one polymorphism address. Thus, which polymorphism pattern in main DB 14 matches with the received polymorphism address and the polymorphism pattern thereof is searched.

In step A14 (SA14), the morbidity rate of large-bowel cancer (semantic information) which is associated with the polymorphism pattern matching the received polymorphism pattern is read out in accordance with processing program 13. Specifically, in step A14, the morbidity rate of large-bowel cancer of a requester can be read out in accordance with the polymorphism address and polymorphism pattern submitted by the requester. The read-out morbidity rate is stored in memory section A10 in association with the requester's "Ono" and "polymorphism address," and "polymorphism pattern," At this time, the morbidity rate of large-bowel cancer may be corrected in accordance with additional information and then stored. Alternatively, other information obtained from additional information may be stored in association with the requester's "Gno."

In step A15 (SA15), the morbidity rate in association with the polymorphism address, which is utilized when reading it from main DB 14, which are stored in memory section A10, are transmitted to personal computer 3 through communication network 1 together with the requester's "Gno.". In step A15, the morbidity rate that has been read out in step A14 is allowed to link with the polymorphism address corresponding thereto and they are transmitted in sets. In addition to the set of "Gno.", the morbidity rate and the polymorphism address corresponding thereto, the "source of information" recorded in main DB 14 may be transmitted in association with a set of the morbidity of rate and the polymorphism address. Transmission of the source of information enables the requester to evaluate the credibility of the morbidity rate based on the source of information, the polymorphism addresses corresponding to the morbidity rate, and the polymorphism pattern corresponding to the polymorphism address. Specifically, in the side of the requester, the received source of information and the received set of the morbidity rate and the polymorphism address corresponding thereto are associated with the polymorphism pattern that had been transmitted by the requester in step A11 and then outputted on display device 22 of personal computer 3 or on paper in step A19 described below. This enables the requester to learn that the organization specified in the source of information had provided information concerning the morbidity rate with the use of the polymorphism pattern that had been associated with the polymorphism address. Thus, the requester can evaluate the credibility of information concerning the morbidity rate. Also, this encourages the provider of information to provide reliable services since the requester evaluates credibility. When the polymorphism pattern associated with the polymorphism address that was provided by the requester has been confirmed previously via informed consent, whether or not the information confirmed via informed consent matches the outputted information can be visually confirmed.

In step A16 (SA16), personal computer 3 receives the requester's "Gno." and the set of the morbidity rate and the polymorphism address corresponding thereto. The set of the received morbidity rate and the polymorphism address corresponding thereto are recorded in memory section 26.

In step A11 (SA17), whether or not the polymorphism address associated with the polymorphism pattern that had been transmitted to shared computer 2 in step A11 matches the polymorphism address contained in the set of the morbidity rate and the polymorphism address corresponding thereto (hereafter referred to as "the polymorphism address received in step A16") that had been received in step A16 is evaluated in step A17 (SA17). When the polymorphism address that had been transmitted in step A11 completely matches the polymorphism address received in step A16, a "yes" evaluation is given in step A17. In contrast, when the polymorphism address that had been transmitted in step A11 does not match the polymorphism address received in step A16, a "no" evaluation is given. An example of a case where the polymorphism address transmitted in step A11 does not match the polymorphism address received in step A16 is a case where at least one polymorphism address among a plurality of polymorphism addresses that had been transmitted in step A11 does not match. The term "match" used herein refers to notational and substantive consistency of polymorphism addresses. Notational consistency of polymorphism addresses means that the notations concerning the given positions in the nucleotide sequences are identical to each other. Substantive consistency of polymorphism addresses means that, for example, the addresses directly or indirectly represent the same position in the nucleotide sequences, even if they are not notationally identical to each other.

When a "no" evaluation is given in step A17, the process is advanced to step A18 (SA18). In contrast, it is advanced to step A19 (SA19) when a "yes" evaluation is given. An alert regarding this is then given via display device 22 and this alert is transmitted to shared computer 2 in step A18, since it was found in step A17 that all the polymorphism patterns related to the polymorphism addresses transmitted in step A11 were not used for acquiring the morbidity rate (semantic information) in shared computer 2. Following step A18, the process is advanced to step A19 described below, and the process is continued. "Alerts" include, for example, a warning that is made based on evaluation that the probability of unauthorized use and acquisition is high, a notification that all the transmitted polymorphism patterns were not used, and an announcement regarding notification to a third party of the fact that all the transmitted polymorphism patterns were not used.

In step A19, the morbidity rate of large-bowel cancer is displayed on display device 22 based on semantic information recorded in memory section 26 in accordance with processing program 27. This enables the requester to acquire the morbidity rate of large-bowel cancer using the genome-related information 28 recorded on genome-related information recording medium 24. When a "yes" evaluation is given in step A17, all the polymorphism patterns associated with the polymorphism addresses transmitted in step A11 were found to have been used for acquiring the morbidity rate (semantic information) in shared computer 2. Following step A17, accordingly, step A19 is executed.

When "information associated with semantic information" is further drawn out from "semantic information" that has been read out in step A14, "semantic information" and "information associated with the semantic information" are transmitted in association with the polymorphism address in step A15, and they are received in step A16, steps A17 and thereafter are carried out in the same manner, and "semantic information" and "information associated with the semantic information" are displayed in step A19.

In this system, in case that information concerning the provision of "functional foods that prevent large-bowel cancer" is further received in step A3 as requested information in addition to "the morbidity rate of large-bowel cancer" requested by the requester when, for example, the morbidity rate exceeds a given standard, information concerning the requested functional foods can be provided together with information concerning the morbidity rate of large-bowel cancer of the requester when the morbidity rate exceeds a given standard.

Steps A3 to A7 and steps up to A12 in shared computer 2 may be carried out with an organization different from that of steps A12 to A15. In such a case, a step that is carried out in shared computer 2 is divided into two steps.

As described above, in this system, utilization of genome-related information recording medium 24, which has individuals' polymorphism patterns in association with polymorphism addresses recorded thereon, enables individuals to use semantic information recorded in main DB 14 through the polymorphism addresses. In other words, an individual utilizing this system does not have to record semantic information on a genome-related information recording medium. Instead, the individual can obtain various semantic information simply by possessing genome-related information 28 having the polymorphism pattern associated with the polymorphism address.

Particularly, in this system, a set of the morbidity rate and a polymorphism address corresponding thereto is received from shared computer 2 in step A16. Based on the polymorphism address received in step A16, whether or not shared computer 2 had used all the polymorphism patterns associated with the polymorphism address that had been transmitted in step A11 for acquiring the morbidity rate (semantic information) is confirmed in step A17.

Specifically, the requester can confirm whether or not shared computer 2 used all the polymorphism patterns associated with the polymorphism address that had been transmitted in step A11 for acquiring semantic information. The requester is able to learn of an unauthorized use, such as the case that, for example, the polymorphism patterns associated with the polymorphism address that had been transmitted in step A11 were used for a purpose other than that of the requester or simply acquired in shared computer 2. When the polymorphism pattern associated with the polymorphism address is used or acquired for purposes other than its original purpose, i.e., presentation of the requested morbidity rate, shared computer 2 cannot conceal such action from the requester.

Accordingly, this system can prevent the unauthorized use and acquisition of the polymorphism addresses and the polymorphism patterns recorded on genome-related information recording medium 24 of shared computer 2.

In this system, an alert that all the polymorphism patterns associated with the polymorphism address that had been transmitted in step A11 were not used for acquiring semantic information in shared computer 2 is shown on display device 22, and this alert is also transmitted to shared computer 2 in step M8. When a "no" evaluation is given in step A17, an alert is preferably transmitted to shared computer 2, and information concerning the shared computer 2 is preferably disclosed to a third party other than the shared computer 2, A third party comprises a database, which stores information obtained from personal computer 3 and a transmitter/receiver for transmitting and receiving information between personal computer 3 and shared computer 2 through communication network 1. An example of a third party is an organization that makes sure that the rules concerning the transmission/reception of genome-related information through communication network I are complied with. A third party may be a public or private organization.

A third party stores the information concerning shared computer 2 that has been transmitted from personal computer 3 in the database. A third party may disclose the stored information concerning shared computer 2 to the public via a transmitter/receiver. Also, it may provide alerts concerning the unauthorized use or acquisition of the polymorphism patterns associated with the polymorphism address and the like to shared computer 2.

Thus, a system for processing information that comprises a third party can more effectively prevent the unauthorized use and acquisition of the polymorphism patterns associated with the polymorphism addresses in shared computer 2.

Meanwhile, in the system for processing information, a recording medium prepared by removing information contained as data II from a genome-related information recording medium; that is, a recording medium having only data I and additionally data III to V, may be used. In this case, information contained as data II is recorded in an external database (genome-related information recording medium) connected to personal computer 3 through communication network 1. In such a system, for example, in the above step A10, the external database is accessed through communication network 1, a polymorphism pattern in the instructed polymorphism address is read out, and the polymorphism pattern can be recorded in association with the polymorphism address in memory section 26. As shown in the process of the flow charts shown in FIGS. 6 and 7, respectively, the requester can obtain semantic information via this system.

The system for processing information may be equipped with genome-related information recording medium 24 connected to personal computer 3 via communication network 1 instead of the requester has genome-related information recording medium 24 or the recording medium prepared by removing information contained in data II from such genome-related information recording medium. In such a system, the requester can access genome-related information recording medium 24 through communication network I to download information such as "polymorphism addresses" and "polymorphism patterns" recorded on genome-related information recording medium 24 into personal computer 3. In this case, genome-related information recording medium 24 may comprise genome-related information of a plurality of individuals (each "Gno.") recorded thereon.

In addition, the present invention is not limited to the above-mentioned construction, i.e., shared computer 2 comprising main DB 14. For example, the present invention is applicable to a system for processing information equipped with main DB 14 connected to shared computer 2 via communication network 1. In this case, shared computer 2 accesses main DB 14 through communication network 1 in a manner as shown in the flow charts shown in FIGS. 6 and 7. In such a case, the requester can also obtain desired semantic information in accordance with the processes of the flow charts shown in FIGS. 6 and 7 according to the system for processing information.

More specifically, shared computer 2 can access a plurality of main DBs 14 owned by different organizations or groups through communication network 1 and can utilize semantic information contained in such plurality of main DBs 14, thereby providing information to the requester. In the system for processing information, shared computer 2 accesses various main DBs 14 containing information concerning the morbidity rate of large-bowel cancer as semantic information in step A4 as shown in the flow charts shown in FIGS. 6 and 7. According to the system for processing information, therefore, the requester can obtain information concerning the morbidity rate of large-bowel cancer from information contained in a plurality of main DBs 14.

In this system, shared computer 2 may transmit at least the requested information received from personal computer 3 to a so-called agent and obtain semantic information ("morbidity rate of large-bowel cancer" in this embodiment) through the agent as shown in the processes of the flow charts shown in FIGS. 6 and 7.

A polymorphism pattern may or may not be encrypted in this system.

For example, an encrypted polymorphism pattern may be received from among the encrypted polymorphism patterns associated with the polymorphism address. A decrypted polymorphism pattern may be received from among the encrypted polymorphism patterns. An encrypted polymorphism pattern may be received from among the unencrypted polymorphism patterns.

Alternatively, an encrypted polymorphism pattern may be acquired and then transmitted in that state. An encrypted polymorphism pattern may be acquired, decrypted, and then transmitted in that state. An unencrypted polymorphism pattern may be acquired, encrypted, and then transmitted in that state.

All publications, patents, and patent applications cited herein are incorporated herein by reference in their entirety.

INDUSTRIAL APPLICABILITY

As is apparent from the foregoing description, the present invention can construct a highly safe system for processing information, which can provide useful semantic information for an individual and/or information associated with the semantic information via effective utilization of differences in nucleotide sequence information among individuals.

What is claimed is:

1. A non-transitory computer readable storage medium containing a computer readable code for operating a computer to perform a method for processing information on nucleotide sequence, the method comprising the steps of:
   (a) receiving positional information representing a position in a nucleotide sequence in accordance with a request for an object and/or service;
   (b) obtaining from a memory device, from among a plurality of pieces of polymorphism pattern, a polymorphism pattern associated with the positional information received in step (a); wherein the obtained polymorphism pattern is information on nucleotide sequence which differs among individual organisms and shows a pattern of nucleotide or nucleotide sequence in a polymorphism;
   (c) transmitting the polymorphism pattern obtained in step (b);
   (d) receiving semantic information corresponding to the polymorphism pattern transmitted in step (c) and/or information associated with the semantic information in association with positional information, wherein the semantic information refers to information on phenotypes caused by one or more differences in polymorphism patterns; and
   (e) making a determination as to whether the positional information received in step (d) matches positional information related to the polymorphism pattern transmitted in step (c);
   wherein step (e) comprises alerting a party that received the polymorphism pattern transmitted in step (c), and wherein the step of alerting is performed in response to the determination made in step (e); and wherein steps (a) through (e) are conducted under the control of a processor.

2. The computer readable storage medium of claim 1, wherein the information on phenotypes caused by one or more differences in polymorphism patterns includes information on responsiveness to medicaments.

3. The computer readable storage medium of claim 1, wherein step (e) further comprises transmitting a warning that is made based on an evaluation that the probability of unauthorized use and acquisition is high, a notification that all the transmitted polymorphism patterns were not used, or an announcement regarding notification to a third party that all the transmitted polymorphism patterns were not used.

4. The computer readable storage medium of claim 1, wherein the step of obtaining the polymorphism pattern includes the step of using the processor to access the memory device.

5. An information processing system for processing information on nucleotide sequence comprising:

a shared computer, the shared computer having a processor configured to:
receive positional information representing a position in a nucleotide sequence in accordance with a request for an object and/or service;
obtain from a memory device, froth among a plurality of pieces of polymorphism pattern, a polymorphism pattern associated with the received positional information, wherein the obtained polymorphism pattern is information on nucleotide sequence which differs among individual organisms and shows a pattern of nucleotide or nucleotide sequence in a polymorphism;
transmit the obtained polymorphism pattern; and
receive semantic information corresponding to the transmitted polymorphism pattern and/or information associated with the semantic information in association with positional information, wherein the semantic information refers to information on phenotypes caused by one or more differences in polymorphism patterns;
make a determination as to whether the received positional information matches positional information related to the transmitted polymorphism pattern; and
in response to making the determination, disclose information concerning a party that received the transmitted polymorphism pattern to a third party,
wherein the third party is an organization for ensuring compliance with rules concerning transmission/reception of positional information or polymorphism pattern through a communication network.

6. The information processing system of claim 5, wherein the information on phenotypes caused by one or more differences in polymorphism patterns includes information on responsiveness to medicaments.

7. A non-transitory computer readable medium encoded with a software program for processing information on nucleotide sequence, said program when executed by an information processing device causing the information processing device to:
(a) receive positional information representing a position in a nucleotide sequence in accordance with a request for an object and/or service;
(b) obtain, from among a plurality of pieces of polymorphism pattern, a polymorphism pattern associated with the positional information received in step (a), wherein the obtained polymorphism pattern is information on nucleotide sequence which differs among individual organisms and shows a pattern of nucleotide or nucleotide sequence in a polymorphism;
(c) transmit the polymorphism pattern obtained in step (b);
(d) receive information corresponding to the polymorphism pattern transmitted in step (c) and/or information associated with the corresponding information in association with positional information; and
(e) make a determination as to whether the positional information received in step (d) matches positional information related to the polymorphism pattern transmitted in step (c); and
wherein, in response to step (e), the device alerts a party that received the polymorphism pattern transmitted in step (c), and wherein steps (a) through (e) are conducted under the control of a processor.

8. The computer readable medium of claim 7, wherein the corresponding information includes information on responsiveness to medicaments, side-effects caused by medicaments, risk of diseases and disorders, diatheses and properties, or interaction among proteins.

9. The computer readable medium of claim 7, wherein step (e) includes determining that there is no match between the positional information received in step (d) and the positional information related to the polymorphism pattern transmitted in step (c).

10. A System for processing information on a nucleotide sequence, the system comprising:
a processor configured to:
receive positional information representing a position in a nucleotide sequence in accordance with a request for an object and/or service;
obtain from a memory device, from among a plurality of pieces of polymorphism pattern, a polymorphism pattern associated with the received positional information, wherein the obtained polymorphism pattern is information on nucleotide sequence which differs among individual organisms and shows a pattern of nucleotide or nucleotide sequence in a polymorphism;
transmit the obtained polymorphism pattern;
receive information corresponding to the transmitted polymorphism pattern and/or information associated with the corresponding information in association with positional information;
make a determination as to whether the received positional information matches positional information related to the transmitted polymorphism pattern; and
disclose information concerning a party that received the transmitted polymorphism pattern to a third party,
wherein the third party is an organization for ensuring compliance with rules concerning transmission/reception of the positional information or the polymorphism pattern through a communication network.

11. The system of claim 10, wherein the corresponding information includes information on responsiveness to medicaments, side-effects caused by medicaments, risk of diseases and disorders, diatheses and properties, or interaction among proteins.

12. The system of claim 10, wherein the processor further determines that there is no match between the received positional information and the positional information related to the transmitted polymorphism pattern.

13. An apparatus for processing information on nucleotide sequence, comprising:
a transmitter/receiver that receives positional information representing a position in a nucleotide sequence in accordance with a request for an object and/or service; and
a CPU that:
obtains from a memory device, from among a plurality of pieces of polymorphism pattern, a polymorphism pattern associated with the positional information received by the transmitter/receiver, wherein the obtained polymorphism pattern is information on nucleotide sequence which differs among individual organisms and shows a pattern of nucleotide or nucleotide sequence in a polymorphism;
causes the transmitter/receiver to transmit the polymorphism pattern obtained from the memory device;
causes the transmitter/receiver to receive semantic information corresponding to the transmitted polymorphism pattern and/or information associated with the semantic information in association with positional information, wherein the semantic information refers to information on phenotypes caused by one or more differences in polymorphism patterns;

makes a determination as to whether the received positional information matches positional information related to the transmitted polymorphism pattern; and causes the apparatus to alert a party that received the transmitted polymorphism pattern, and wherein the causing of the apparatus to alert is performed in response to the determination as to whether the received positional information matches positional information related to the transmitted polymorphism pattern.

14. The apparatus of claim 13, wherein the information on phenotypes caused by one or more differences in polymorphism patterns includes information on responsiveness to medicaments.

15. The apparatus of claim 13, wherein the information on phenotypes caused by one or more differences in polymorphism patterns includes information on side-effects caused by medicaments.

16. The apparatus of claim 13, wherein the information on phenotypes caused by one or more differences in polymorphism patterns includes information on risk of diseases and disorders.

17. The apparatus of claim 13, wherein the information on phenotypes caused by one or more differences in polymorphism patterns includes information on diatheses and properties.

18. The apparatus of claim 13, wherein the information on phenotypes caused by one or more differences in polymorphism patterns includes information on interaction among proteins.

19. The apparatus of claim 13, wherein the apparatus is arranged to transmit a warning that is made based on an evaluation that the probability of unauthorized use and acquisition is high, a notification that all the transmitted polymorphism patterns were not used, or an announcement regarding notification to a third party that all the transmitted polymorphism patterns were not used.

20. An apparatus for processing information on nucleotide sequence, comprising:
a transmitter/receiver for receiving positional information representing a position in a nucleotide sequence in accordance with a request for an object and/or service; and
a CPU that:
obtains from a memory device, from among a plurality of pieces of polymorphism pattern, a polymorphism pattern associated with the positional information received by the transmitter/receiver, wherein the obtained polymorphism pattern is information on nucleotide sequence which differs among individual organisms and shows a pattern of nucleotide or nucleotide sequence in a polymorphism;
causes the transmitter/receiver to transmit the obtained polymorphism pattern;
causes the transmitter/receiver to receive semantic information corresponding to the transmitted polymorphism pattern and/or information associated with the semantic information in association with positional information, wherein the semantic information refers to information on phenotypes caused by one or more differences in polymorphism patterns;
makes a determination as to whether the received positional information matches positional information related to the transmitted polymorphism pattern; and
causes the apparatus to disclose information concerning a party that received the transmitted polymorphism pattern, and wherein the third party is an organization for ensuring compliance with rules concerning transmission/reception of positional information or polymorphism pattern through a communication network, and wherein the causing of the apparatus to disclose is performed in response to the determination as to whether the received positional information matches positional information related to the transmitted polymorphism pattern.

21. The apparatus of claim 20, wherein the information on phenotypes caused by one or more differences in polymorphism patterns includes information on responsiveness to medicaments.

22. The apparatus of claim 20, wherein the information on phenotypes caused by one or more differences in polymorphism patterns includes information on side-effects caused by medicaments.

23. The apparatus of claim 20, wherein the information on phenotypes caused by one or more differences in polymorphism patterns includes information on risk of diseases and disorders.

24. The apparatus of claim 20, wherein the information on phenotypes caused by one or more differences in polymorphism patterns includes information on diatheses and properties.

25. The apparatus of claim 20, wherein the information on phenotypes caused by one or more differences in polymorphism patterns includes information on interaction among proteins.

26. The apparatus of claim 20, wherein the apparatus is arranged to transmit a warning that is made based on an evaluation that the probability of unauthorized use and acquisition is high, a notification that all the transmitted polymorphism patterns were not used, or an announcement regarding notification to a third party that all the transmitted polymorphism patterns were not used.

27. The computer readable storage medium of claim 1, wherein the information on phenotypes caused by one or more differences in polymorphism patterns includes information on side-effects caused by medicaments.

28. The computer readable storage medium of claim 1, wherein the information on phenotypes caused by one or more differences in polymorphism patterns includes information on risk of diseases and disorders.

29. The computer readable storage medium of claim 1, wherein the information on phenotypes caused by one or more differences in polymorphism patterns includes information on diatheses and properties.

30. The computer readable storage medium of claim 1, wherein the information on phenotypes caused by one or more differences in polymorphism patterns includes information on interaction among proteins.

31. The information processing system of claim 5, wherein the information on phenotypes caused by one or more differences in polymorphism patterns includes information on side-effects caused by medicaments.

32. The information processing system of claim 5, wherein the information on phenotypes caused by one or more differences in polymorphism patterns includes information on diatheses and properties.

33. The information processing system of claim 5, wherein the information on phenotypes caused by one or more differences in polymorphism patterns includes information on interaction among proteins.

* * * * *